US012629097B2

(12) United States Patent
Wolfe

(10) Patent No.: US 12,629,097 B2
(45) Date of Patent: May 19, 2026

(54) SENSOR AND CANNULA

(71) Applicant: PercuSense, Inc., Valencia, CA (US)

(72) Inventor: Katherine Wolfe, Dunwoody, GA (US)

(73) Assignee: PercuSense, Inc., Valencia, CA (US)

( * ) Notice: Subject to any disclaimer, the term of this patent is extended or adjusted under 35 U.S.C. 154(b) by 0 days.

(21) Appl. No.: 17/187,571

(22) Filed: Feb. 26, 2021

(65) Prior Publication Data

US 2021/0267548 A1      Sep. 2, 2021

Related U.S. Application Data

(60) Provisional application No. 63/047,018, filed on Jul. 1, 2020, provisional application No. 62/983,426, filed on Feb. 28, 2020.

(51) Int. Cl.

| | |
|---|---|
| *A61B 5/00* | (2006.01) |
| *A61B 5/145* | (2006.01) |
| *A61B 5/1473* | (2006.01) |
| *A61F 2/02* | (2006.01) |
| *A61M 5/172* | (2006.01) |
| *A61M 25/00* | (2006.01) |

(52) U.S. Cl.
CPC ........ *A61B 5/6852* (2013.01); *A61B 5/14532* (2013.01); *A61B 5/14546* (2013.01); *A61B 5/1473* (2013.01); *A61B 2562/04* (2013.01);

*A61F 2/022* (2013.01); *A61M 5/1723* (2013.01); *A61M 25/001* (2013.01); *A61M 2205/6036* (2013.01)

(58) Field of Classification Search
CPC .............. A61B 5/6852; A61B 2562/04; A61B 5/14532; A61B 5/14546; A61B 5/1473; A61B 5/6848; A61M 25/001; A61M 2205/6036; A61M 5/1723; A61M 5/158; A61M 2005/1588; A61F 2/022
See application file for complete search history.

(56) References Cited

U.S. PATENT DOCUMENTS

2019/0216371 A1* 7/2019 Shah .................... A61B 5/6852
2021/0244359 A1* 8/2021 Schloesser ............. G16H 40/67

* cited by examiner

*Primary Examiner* — Charles A Marmor, II
(74) *Attorney, Agent, or Firm* — PercuSense, Inc.

(57) ABSTRACT

In one embodiment, an integrated cannula and sensor assembly is disclosed. The integrated cannula and sensor assembly includes a cannula with a proximal end and a distal end. The cannula also has a body and a tip. The body includes a channel and a body distal that is defined between the proximal end and the distal end. The tip is defined between the body distal and the distal end. The assembly further includes a sensor assembly that is located within the channel, wherein the tip further includes an undercut configured to retain the sensor assembly.

18 Claims, 6 Drawing Sheets

SENSOR AND CANNULA

RELATED APPLICATIONS

This application claims the benefit of U.S. provisional application numbers: 62/983,426 filed Feb. 28, 2020; and 63/047,018 filed Jul. 1, 2020. The applications listed above are hereby incorporated by reference in their entirety for all purposes.

FIELD OF THE INVENTION

The present invention is generally directed to devices and methods that perform in vivo monitoring of an analyte or analytes such as, but not limited glucose, lactate or ketones. In particular, the devices and methods are for electrochemical sensors that provide information regarding the presence or amount of an analyte or analytes within a subject.

BACKGROUND OF THE INVENTION

Diabetes is a growing healthcare crisis, affecting nearly 30 million people in the United States. Approximately 10 percent of those affected require intensive glucose and insulin management. In hospital patients, hypoglycemia in both diabetic and non-diabetic patients is associated with increased cost and short- and long-term mortality.

Diabetes and other diseases may be treated by obtaining information about analytes such as glucose, as well as obtaining information about other physiological properties. Diabetes and other diseases may be treated by delivering an infusate, such as insulin and other agents.

Obtaining information about analytes and/or other physiological properties may be performed using one or more sensors implanted in a subject. For example, obtaining information about glucose concentration may be performed using a glucose sensor implanted in a subject. Sensors may kink, fold, and break during insertion and wear. Also, sensors implanted for prolonged periods of time may lead to a stagnant sensor-tissue interface.

Delivering an infusate may be performed using a catheter implanted in a subject. An implantation site for a catheter may be separate from an implantation site for a sensor. Multiple implantation sites for a catheter and a sensor may use more space and may cause more trauma.

What is needed are in vivo sensing devices with sensors that resist kinking, folding, and breaking. What is also needed are in vivo sensing devices that reduce the likelihood of a stagnant sensor-tissue interface. What is also needed are sensing and infusion devices that are able to both (1) sense an analyte and/or physiological property and (2) deliver an infusate, with fewer implantation sites, such as a single implantation site.

BRIEF SUMMARY OF THE INVENTION

In one embodiment, an integrated cannula and sensor assembly is disclosed. The integrated cannula and sensor assembly includes a cannula with a proximal end and a distal end. The cannula also has a body and a tip. The body includes a channel and a body distal that is defined between the proximal end and the distal end. The tip is defined between the body distal and the distal end. The assembly further includes a sensor assembly that is located within the channel, wherein the tip further includes an undercut configured to retain the sensor assembly.

In another embodiment, an integrated cannula and sensor assembly is disclosed that includes a cannula with a proximal end and a distal end. The cannula includes a body and a tip where the body has a first channel, a second channel, and a body distal. The body distal is between the proximal end and the distal end and the tip is between the body distal and the distal end. The integrated cannula and sensor assembly further includes a first sensor assembly located within the first channel and a second sensor assembly located within the second channel. Wherein the tip further includes a first undercut that retains the first sensor assembly and a second undercut that retains the second sensor assembly.

Other features and advantages of the invention will become apparent from the following detailed description, taken in conjunction with the accompanying drawings that illustrate, by way of example, various features of embodiments of the invention.

DETAILED DESCRIPTION

Figure 1:
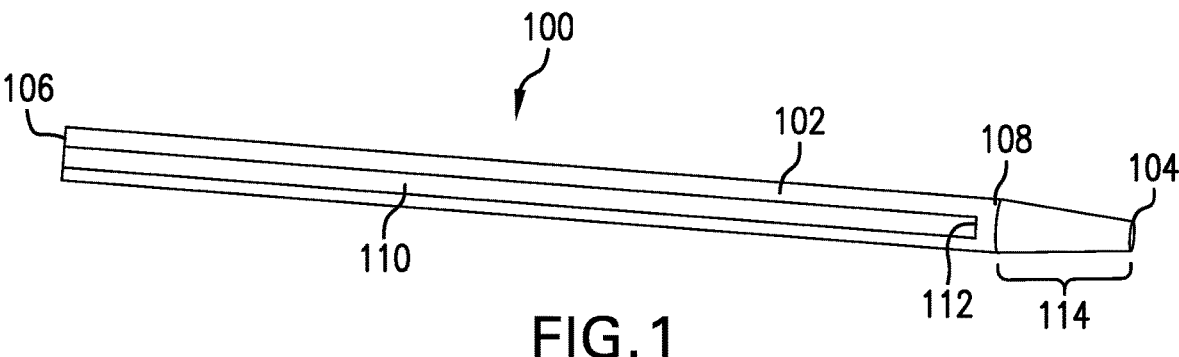
FIG. 1 is an exemplary pseudo-isometric illustration of a cannula in accordance with embodiments of the present invention.

Presented below are embodiments that are intended to enable a combined infusion set and sensor. In the embodiments presented below a cannula to deliver an infusate is configured to accommodate at least one sensor assembly. In many embodiments the infusion cannula is configured to accommodate a plurality of sensor assemblies. The combination of an infusion cannula and sensor can simplify the use of artificial pancreas systems that require a glucose sensor and infusion set. Simplifying use of an artificial pancreas system can improve adoption rates and promote long term use of the system. In many embodiments a flexible sensor assembly is incorporated with the cannula. In preferred embodiments the flexible sensor can be double backed upon itself such as, but not limited to s-shapes or u-shapes without breaking or compromising sensor performance.

The combined cannula and sensor or sensors is not limited to use with artificial pancreas systems. Additional embodiments can include a single sensor, or multiple sensors, such as, but not limited to electrochemical sensors configured to measure analytes such as lactate, ketones, reactive oxygen, oxygen and the like. Still other embodiments include a plurality of sensors that are configured to measure multiple analytes using a single sensor assembly, such as, but not limited to combinations of glucose, lactate, oxygen, reactive oxygen and ketones. Similarly, the cannula may be configured to deliver infusion fluids other than insulin. In various embodiments the combined cannula and sensor can be used to infuse fluids such as intravenous fluid or medicinal fluids such as, but not limited to pain medications or liquid nutrition. Likewise, while insulin delivery via infusion is typically delivered within the subcutaneous tissue of a subject, in alternative embodiments the combined infusion set and sensor can be used in systems such as, but not limited to, the venous system, musculature organs and the like.

In many embodiments the combined cannula and sensor is placed within a subject using a single sharp configured to pierce the skin of a subject. In many embodiments the sharp may be a hollow or solid needle or any other device capable of piercing the skin to a subject. In other embodiments the sharp may be a lancet or the like. The specific embodiments of sharps disclosed are intended to be exemplary and should not be construed as limiting. Any device capable of piercing the skin of a subject to enable placement of the combined cannula and sensor should be construed as within the scope of this disclosure.

The various embodiments discussed below should not be viewed as discrete embodiments. Rather, it is intended that various elements or components of the various embodiments are intended to be combined with elements, features or components of the other embodiments. While embodiments and examples may be related to particular figures the scope of the disclosure and claims should not be construed to be limited to the explicit embodiments discussed. Rather it should be recognized that various combinations of features, elements and components can be interchanged, combined and even subtracted to enable other embodiments capable of delivering a combined cannula and sensor via a single point of insertion capable of assisting in the diagnosis and monitoring of various metabolic conditions or general physiological health.

FIG. 1 is an exemplary pseudo-isometric illustration of a cannula 100 in accordance with embodiments of the present invention. The cannula 100 has a distal end 104 and a proximal end 106. Between the distal end 104 and the proximal end 106 are a body 102 and a tip 114. The body 102 includes a body distal 108. In many embodiments the body distal 108 is located where the body 102 and the tip 114 meet. The body 102 further includes a channel 110 being sized to accommodate a sensor assembly (not shown) within the channel 110. In many embodiments the channel 110 extends along the length of the body 102 from the proximal end 106 to the body distal 108. In many embodiments, the channel 110 is terminated at a channel distal 112 that is coincident with the body distal 108. In other embodiments, the channel distal 112 terminates at a location that is different from the body distal 108.

The tip 114 of the cannula 100 can be formed in a variety of ways. In one embodiment the tip 114 is formed by tapering a wall thickness resulting in the distal end 104 having a smaller cross-sectional area than the body distal 108. In other embodiments, the tip 114 can be coupled or affixed to the body distal 108 using techniques such as, but not limited to, adhesives, ultrasonic welding, heat staking or the like. The examples discussed above are intended to be exemplary rather than limiting.

Figure 2:
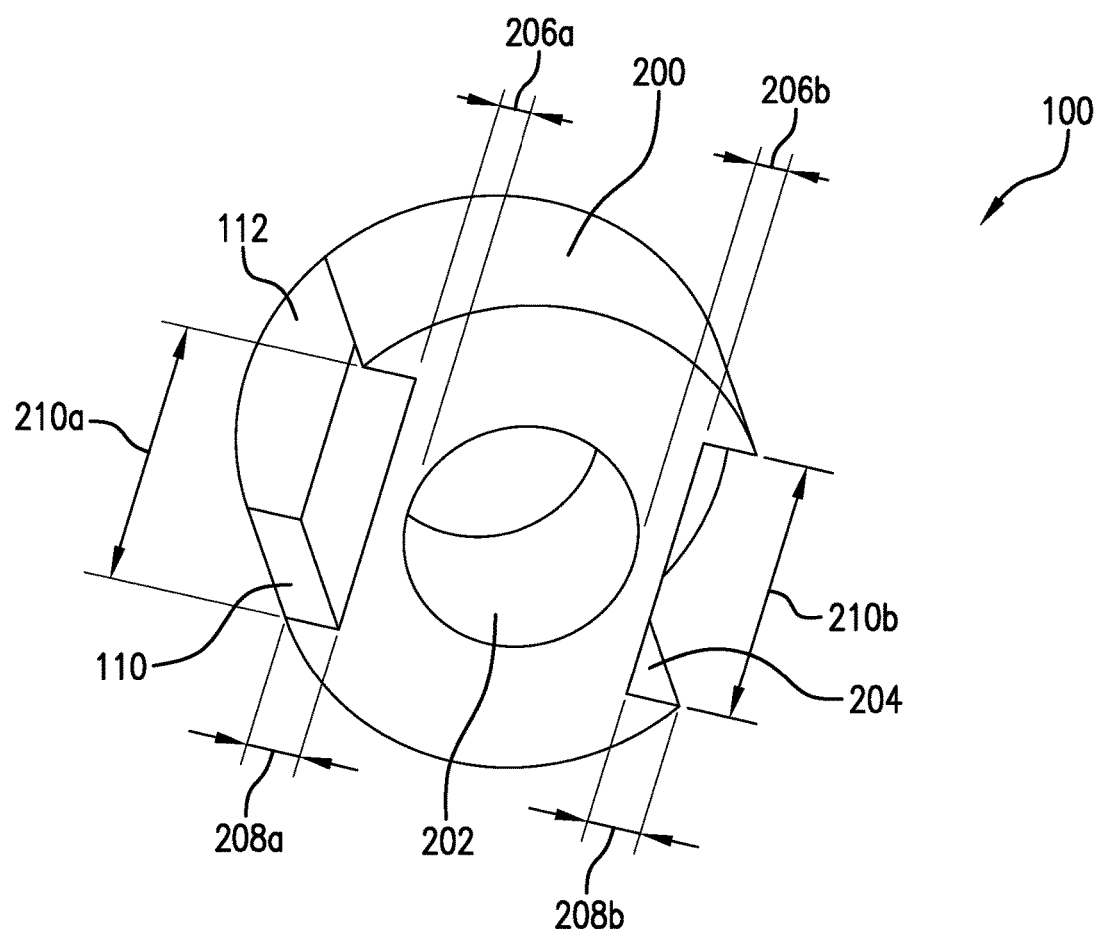
FIG. 2 is an exemplary illustration of a cross-section of a portion of an exemplary cannula, in accordance with embodiments of the present invention.

FIG. 2 is an exemplary illustration of a cross-section of a portion of an exemplary cannula 100, in accordance with embodiments of the present invention. The embodiment illustrated in FIG. 2 has an elliptical, ellipsoid, or substantially elliptical cross-section. One benefit of having the elliptical cross-section includes the ability to create the channel 110 having a depth 208a within the cannula sidewall while maintaining a functional wall thickness 206a for a fluid path 202 within a body 200.

In many embodiments the channel 110 is formed using an extrusion process during the forming of the body 200 of the cannula. As a non-limiting example, consider an extrusion operation that forms the body 200, the fluid path 202 and also the channel 110. In alternative embodiments, the channel 110 is formed using a machining process that removes material from a previously extruded body 200 and fluid path 202. For example, an extrusion operation is performed that formed the body 200 and the fluid path 202. The formation of the body 200 and the fluid path 202 creating a sidewall where the channel 110 will be formed. A subsequent operation such as, but not limited to milling, routing, or skiving forms the channel 110 within the sidewall of the body 200 at the depth 208a, leaving a wall thickness 206a between the channel 110 and the fluid path 202. In alternative embodiments the body 200, the fluid path 202 and the channel 110 may be formed in individual operations or various combinations thereof.

In FIG. 2, the cross-section of the channel 110 is illustrated as being substantially rectangular. However, in various embodiments, different processes used to form the channel 110 can produce different channel 110 cross-section shapes. Non-limiting examples include, but are not limited to elliptical, rectangular, spheroid, v-shaped, w-shaped, or other shapes capable of being formed during an extrusion or material removal process.

In many embodiments the cannula 100 includes the channel 110 and a second channel 204. The second channel 204 may be used to accommodate a second sensor assembly within the cannula 100. Accordingly, the second channel 204 may also be formed in the body 200 of the cannula 100. The second channel 204 can be formed to a depth 208b creating a wall thickness 206b between the second channel 204 and the fluid path 202. The second channel 204 can be formed using similar or different processes than those used to create the channel 110. Likewise, the depth 208b of the second channel 204 may be different from the depth 208a of the channel 110. Accordingly, the wall thickness 206b between the second channel 204 and the fluid path 202 may also differ from the wall thickness 206a between the channel 110 and the fluid path 202.

The channel 110 has a width 210a and the second channel 204 has a width 210b. In many embodiments the width 210a and the width 210b are the same. In other embodiments, the width 210a and the width 210b are different. Differences between the widths 210a and 210b, and depths 208a and 208b can be based on physical properties of the sensor assembly that is intended to be placed within the respective channels. The channel 110 and the second channel 204 may have different depths 208a and 208b as well as different widths 210a and 210b. Accordingly, the respective channels 110 and 204 may accommodate sensor assemblies having different sizes. It may be advantageous to accommodate sensor assemblies of different sizes for a multitude of reasons. Exemplary, non-limiting advantages of being able to accommodate different sensor assembly sizes include, but are not limited to sensor assemblies having the capability to measure multiple analytes, redundant sensor assemblies, separation of sensor assembly components such as working electrodes, counter electrodes, reference electrodes or combination counter/reference electrodes. In various embodiments, it may be advantageous to separate sensor components onto separate sensor assemblies to electrically or physically isolate the sensor components.

The embodiments and examples discussed above are intended to be exemplary rather than limiting. Furthermore, the embodiments and examples should not be construed as discrete embodiments. Rather, the embodiments discussed should be considered as having features that can be combined, substituted or removed from various other embodiments.

Figure 3A:
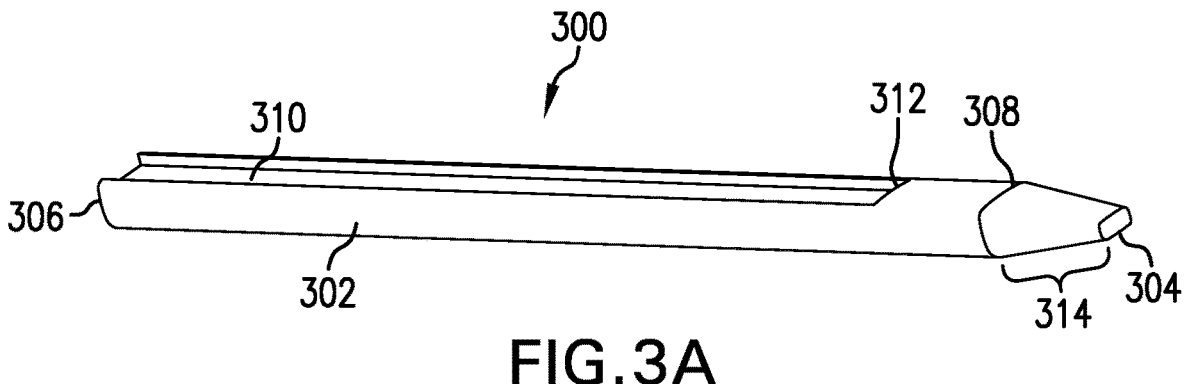
FIG. 3A is an exemplary illustration of an alternative embodiment of a cannula, in accordance with embodiments of the present invention.

FIG. 3A is an exemplary illustration of an alternative embodiment of a cannula 300, in accordance with embodiments of the present invention. Similar to the embodiment described in FIG. 1 the cannula 300 has a distal end 304 and a proximal end 306. Between the distal end 304 and the proximal end 306 are a body 302 and a tip 314. The body 302 includes a body distal 308. The body distal 308 is where the body 302 and the tip 314 meet. The body 302 further includes a channel 310 being sized to accommodate a sensor assembly within the channel 310.

In many embodiments the channel 310 extends along the length of the body 302 from the proximal end 306 to the body distal 308. In many embodiments, the channel is terminated at a channel distal 312 that is coincident with the body distal 308. In other embodiments, such as the one illustrated in FIG. 3A, the channel distal 312 terminates at a location that is different from the body distal 308.

The tip 314 of the cannula 300 can be formed in a variety of ways. In one embodiment the tip 314 is formed by tapering a wall thickness resulting in the distal end 304 having a smaller cross-sectional area than the body distal 308. In other embodiments, the tip 314 can be coupled or affixed to the body distal 308 using techniques such as, but not limited to, adhesives, ultrasonic welding, heat staking or the like. The examples discussed above are intended to be exemplary rather than limiting and other coupling or affixing methods or techniques may be used to secure the tip 314 to the body 302.

Figure 3B:
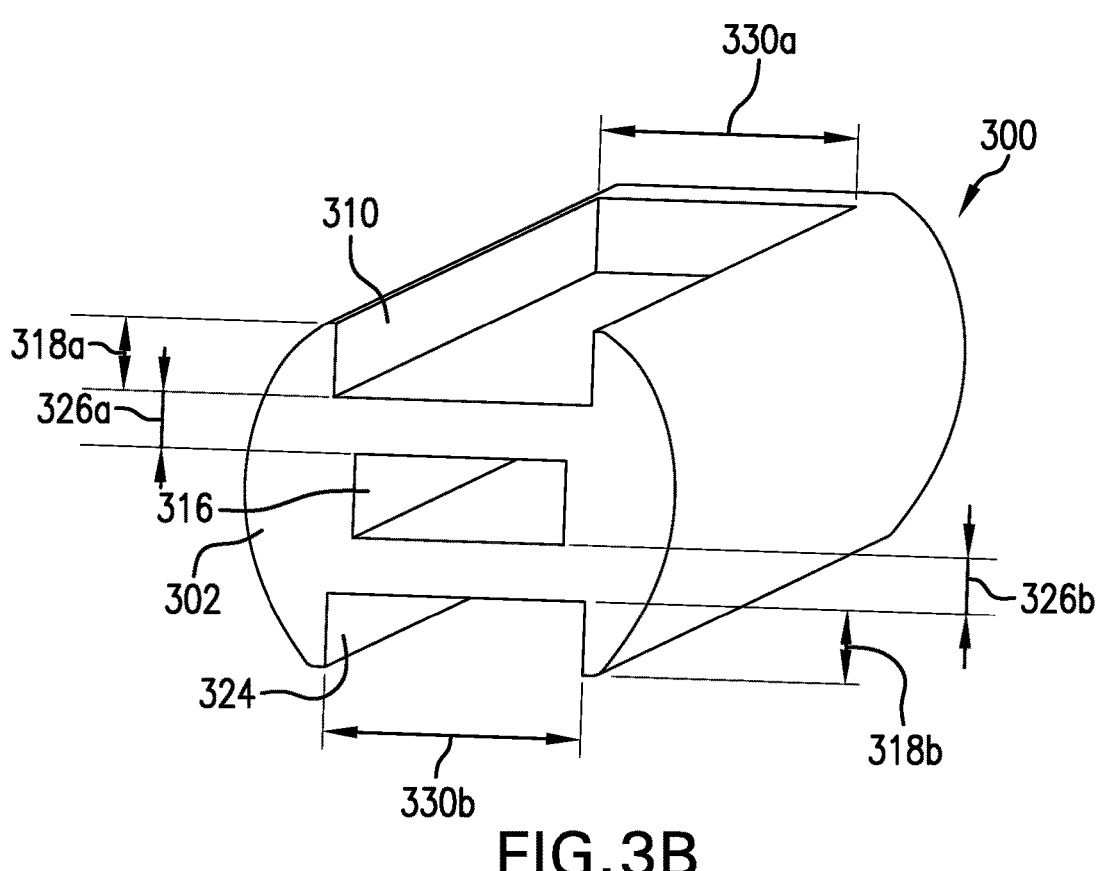
FIG. 3B is an exemplary illustration of a cross-section of an exemplary cannula, in accordance with embodiments of the present invention.

FIG. 3B is an exemplary illustration of a cross-section of an exemplary cannula 300, in accordance with embodiments of the present invention. The embodiment illustrated in FIG. 3B has a substantially rectangular cross-section. One benefit of having the substantially rectangular cross-section includes the ability to create the channel 310 having a depth 318a within the cannula sidewall while maintaining a functional wall thickness 326a for a fluid path 316 within a body 302.

In many embodiments the channel 310 is formed using an extrusion process during the forming of the body 302 of the cannula. As a non-limiting example, consider an extrusion operation that forms the body 302, the fluid path 316 and the channel 310. In alternative embodiments, the channel 310 is formed using a machining process that removes material from a previously extruded body 302. For example, an extrusion operation is performed that forms the body 302 and the fluid path 316. The formation of the body 302 and the fluid path 316 creates a sidewall where the channel 310 will be formed. A subsequent operation such as, but not limited to milling, routing, or skiving forms the channel 310 within the sidewall of the body 302 at the depth 318a, leaving a wall thickness 326a between the channel 310 and the fluid path 316.

In FIGS. 3A and 3B, the cross-section of the channel 310 is illustrated as being substantially rectangular. However, in various embodiments, the process that forms the channel 310 can produce different channel 310 cross-section shapes.

Non-limiting examples include, but are not limited to elliptical, rectangular, spheroid, v-shaped, w-shaped, or other shapes capable of being formed during an extrusion or materials removal process.

In many embodiments the cannula 300 includes the channel 310 and a second channel 324. The second channel 324 may be used to accommodate a second sensor assembly within the cannula 300. Accordingly, the second channel 324 may also be formed in the body 302 of the cannula 300. The second channel 324 can be formed to a depth 318b creating a wall thickness 326b between the second channel 324 and the fluid path 316. The second channel 324 can be formed using similar or different processes than those used to create the channel 310. Likewise, the depth 318b of the second channel 324 may be different from the depth 318a of the channel 310. Accordingly, the wall thickness 326b between the second channel 324 and the fluid path 316 may also differ from the wall thickness 326a between the channel 310 and the fluid path 316.

The channel 310 has a width 330a and the second channel 324 has a width 330b. In many embodiments the width 330a and the width 330b are the same. In other embodiments, the width 330a and the width 330b are different. Differences between the widths 330a and 330b, and depths 318a and 3188b can be based on physical properties of the sensor assembly that is intended to be placed within the respective channels. As the channel 310 and the second channel 324 may have different depths 318a and 3188b as well as different widths 330a and 330b, the respective channels 310 and 324 may accommodate sensor assemblies of different sizes. It may be advantageous to accommodate sensor assemblies of different sizes for a multitude of reasons. Exemplary, non-limiting advantages of being able to accommodate different sensor assembly sizes include, but are not limited to sensor assemblies having the capability to measure multiple analytes, redundant sensor assemblies, separation of sensor assembly components such as working electrodes, counter electrodes, reference electrodes or combination counter/reference electrodes. In various embodiments, it may be advantageous to separate sensor components onto separate sensor assemblies to electrically or physically isolate the sensor components.

Figure 4A:
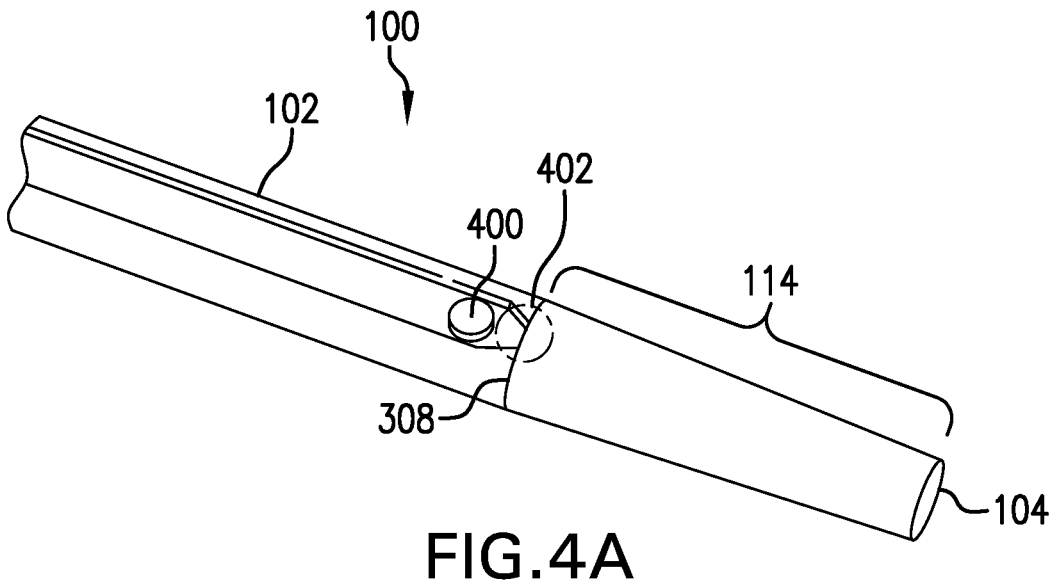
FIGS. 4A and 4B are illustrations of exemplary locating features and key features, in accordance with embodiments of the present invention.
Figure 4B:
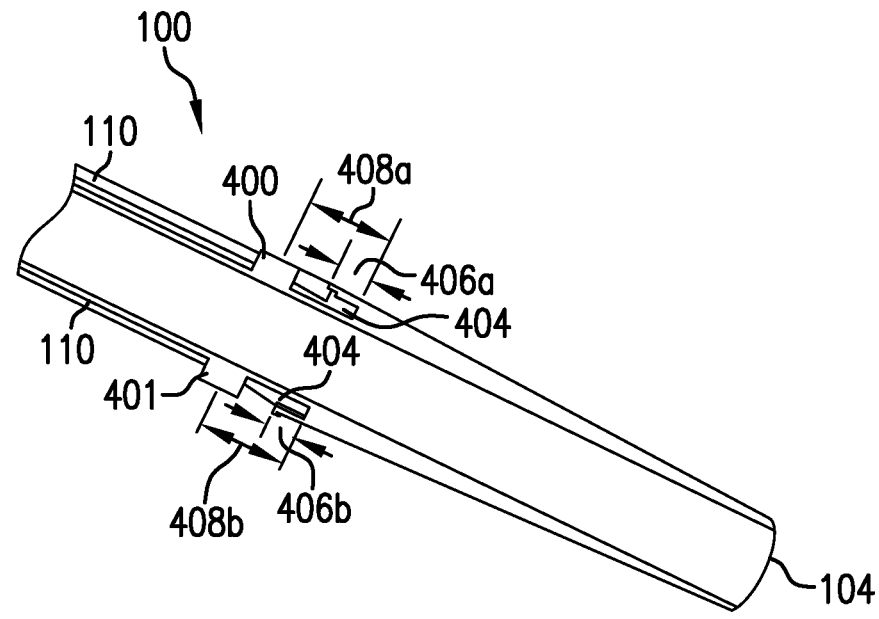

FIGS. 4A and 4B are illustrations of exemplary locating features 400 and key features 402, in accordance with embodiments of the present invention. FIG. 4A is an exemplary pseudo isometric illustration of a portion of the body 102 and the tip 114 of a cannula 100 that further includes locating feature 400 along with key feature 402. FIG. 4B is an exemplary illustration of a cross-section of the cannula 100 found in FIG. 4A. The cross-section in FIG. 4B illustrates how a tipping operation can form the key feature 402.

In FIG. 4A and FIG. 4B the locating feature 400, 401 is a circular boss within the channel 110. The purpose of the locating feature 400, 401 is to interface with a complimentary feature on a sensor assembly (not shown). The circular shape of the locating feature 400, 401 should not be construed as limiting as other embodiments can use other geometric shapes such as polygons or other shapes. In some embodiments the locating feature 400, 401 is formed using a stamping operation or other operation that removes material from the cannula 100 to form the locating feature 400, 401 within the channel 110. In embodiments where the locating feature 400, 401 is a boss that interfaces with a sensor assembly, the locating feature may optionally be used to couple the cannula 100 and the sensor assembly together. In many embodiments a friction fit between the locating feature 400, 401 and exemplary operations to couple the cannula 100 and the sensor assembly include, but are not limited to staking, heat staking, ultrasonic welding and the like.

The exemplary key feature 402 illustrated in FIGS. 4A and 4B are intended to interface with the sensor assembly (not shown) to ensure the sensor assembly is installed having a desired orientation within the cannula 100. In FIG. 4A, the key feature 402 is illustrated as a tapering of the channel 110. The portion of the sensor assembly being configured to be complementary to the geometry of the key feature 402. In FIG. 4B, the cross-section reveals an embodiment having multiple channels 110. Each channel 110 has a key feature 404 that is illustrated as undercut 406a and 406b. Undercut 406a and 406b are intended to be used to retain a portion of the sensor assembly within the channel 110. In some embodiments the key feature 404 is formed using a stamping operation that may be a different operation or performed as part of the same stamping operation that forms the locating feature 400. Alternatively, in other embodiments, such as where the tip 114 is coupled to the body 102, the undercuts 406a and 406b are formed during the coupling of the body 102 to the tip 114.

In embodiments having multiples channels 110, such as those illustrated in FIG. 4B, key features 404 may be differentiated from each other by having undercut 406a be different than undercut 406b. Differentiating undercut 406a from undercut 406b can result in distance 408a (defined between locating feature 400 and the undercut 406a) and distance 408b (defined between locating feature 401 and the undercut 406b) being different. Differentiating distance 408a and distance 408b enables additional locating and keying features to ensure sensor assemblies are placed in the proper channel within the cannula.

Similarly to the locating feature 400, 401 discussed above, the key feature 404 may also be optionally used to coupled the sensor assembly to the cannula 100. A portion of the sensor assembly placed within the undercut 406a/406b may be secured to the cannula using operations such as, but not limited to heat staking, ultrasonic welding, adhesives and the like.

Figure 5:
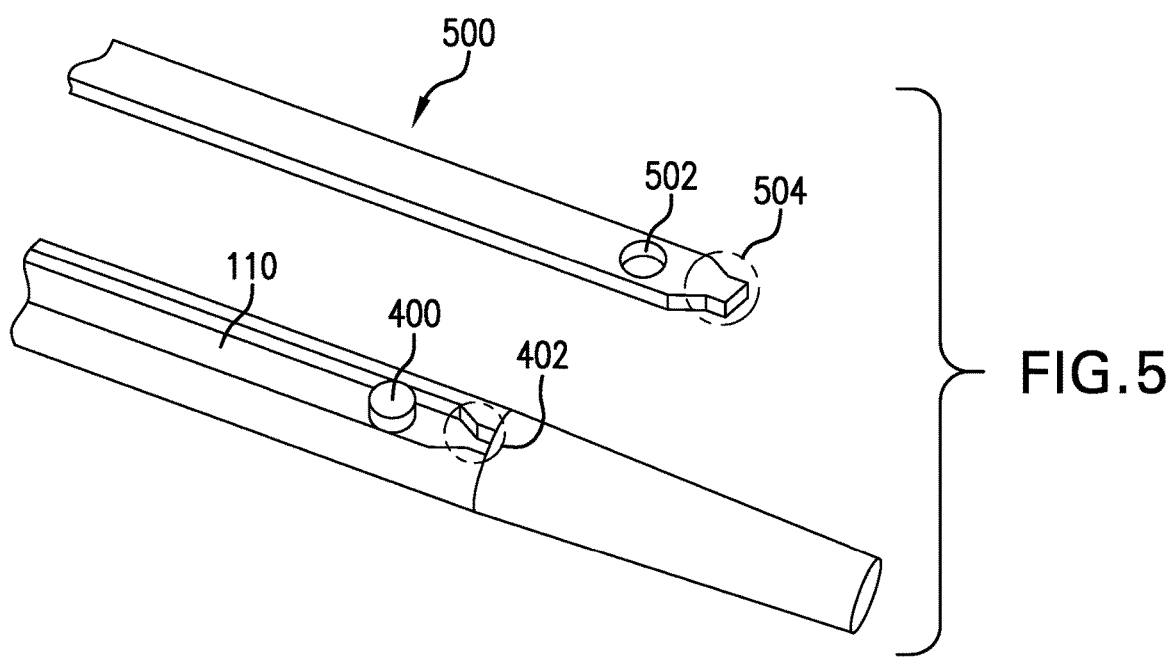
FIGS. 5 and 6 are exemplary illustrations of portions of sensor assemblies configured to be placed within channels formed in cannulas, in accordance with embodiments of the present invention.
Figure 6:
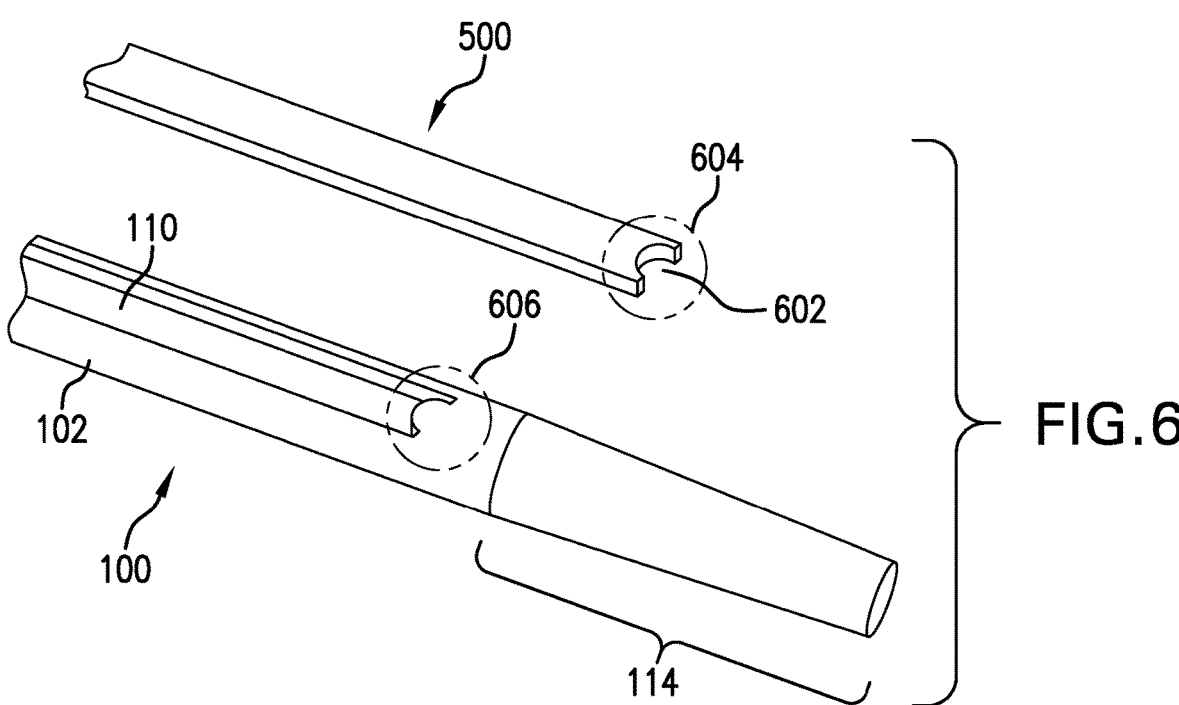

FIGS. 5 and 6 are exemplary illustrations of portions of sensor assemblies 500 configured to be placed within channels 110 formed in cannulas 100, in accordance with embodiments of the present invention. FIG. 5 and FIG. 6 include individual sensor assemblies 500 however as previously illustrated, cannulas 100 may be configured to accommodate one or more sensor assemblies. Each of the sensor assemblies 500 are intended to be placed in channels 110 formed in the respective cannulas 100 shown in FIG. 5 and FIG. 6. Alternatively, in other embodiments a cannula having multiple channels may include a single sensor assembly placed in one of the multiple channels.

In FIG. 5 the sensor assembly 500 includes both a locating feature 502 and a key feature 504. The locating feature 502 and the key feature 504 are intended to interface or interact with locating feature 400 and key feature 402 on the cannula 100. For example, the locating feature 502, illustrated as an aperture in the sensor assembly 500 is intended to be aligned with the locating feature 400 of the cannula 100. In some embodiments a friction fit between the locating feature 400 and the locating feature 502 locates the sensor assembly 500 relative to the cannula 100.

As illustrated, the sensor assembly 500 also includes an optional key feature 504. In embodiments where the sensor includes key feature 504, the cannula 100 may include key feature 402. The key feature 504 is intended to interface or interact with the key feature 402 to promote or ensure a desired orientation of the sensor assembly 500 relative to the cannula 100. While the key feature 504 illustrated in the FIG. 5 may include axial symmetry, other embodiments may be axially asymmetrical to ensure the sensor assembly 500 is properly oriented relative to the cannula 100.

Exemplary embodiments of the key feature 402 formed as part of the cannula 100 are intended to accommodate the key feature 504 of the sensor assembly. As previously discussed regarding FIG. 4B, some embodiments of the key feature 402 include an undercut. The undercut being able to accommodate the key feature 504 of the sensor assembly 500. In many embodiments, placing the key feature 504 beneath the undercut portion of the key feature 402 locates and secures the sensor assembly 500 with the cannula 100. Securing or coupling the sensor assembly 500 to the cannula 100 does not require an undercut feature as part of the key feature 402. In many embodiments, the channel 110 is formed having a width and depth that secures the sensor assembly 500 within the channel 110 via a friction fit. Alternatively, other techniques such as, but not limited to, adhesives, heat staking, ultrasonic welding or the like may be used to couple the sensor assembly 500 with the cannula 100.

In FIG. 6 the sensor assembly 500 includes an alternative embodiment of a key feature 604. The key feature 604 incorporates a geometric shape at the distal end of the sensor assembly 500. The key feature 604 is intended to interface with a key feature 606 on the cannula 100. The key feature 606 is complementary to the key feature 604. In some embodiments the key feature 606 includes an undercut that may be formed when the tip 114 is coupled to the body 102. In many embodiments the undercut enables the sensor assembly 500 to be coupled to the cannula 100 via an operation such as, but not limited to heat staking, ultrasonic welding, adhesives, mechanical fasteners and the like.

Though illustrated as discrete and separate embodiments, the locating features locating features 400, 401 and 502 along with the key features 504, 604, 402 and 606 may be incorporated on a single cannula 100 with multiple channels 110. For example, an assembly may include multiple sensor assemblies 500 and a single cannula 100 having multiple channels 110. In this embodiment, a first sensor assembly 500 may include a locating feature 502 and key feature 504 while the corresponding first channel 110 includes a corresponding locating feature 400 and a key feature 402. A second sensor assembly 500 may include one or both of a second (optionally different) locating feature 502 and key feature 504. Having different locating feature 502 and key features 504 can ensure sensor assemblies are positioned correctly relative to each other when secured to the cannula 100.

Figure 7A:
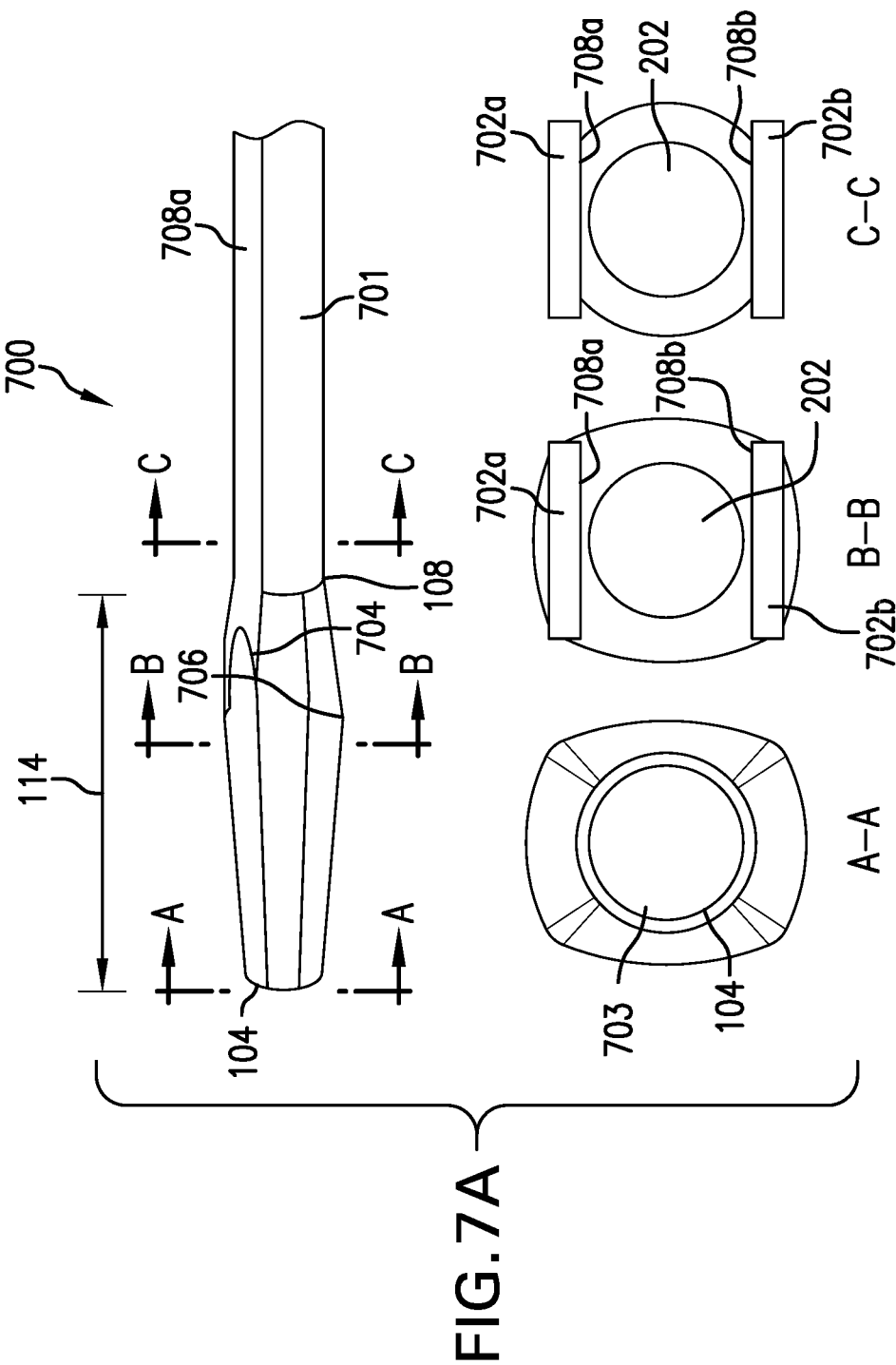
FIGS. 7A and 7B include exemplary illustrations that include a pseudo-perspective view along with at least one cross-section view of alternative embodiments of cannulas configured to accommodate one or more sensors in accordance with embodiments of the present invention.
Figure 7B:
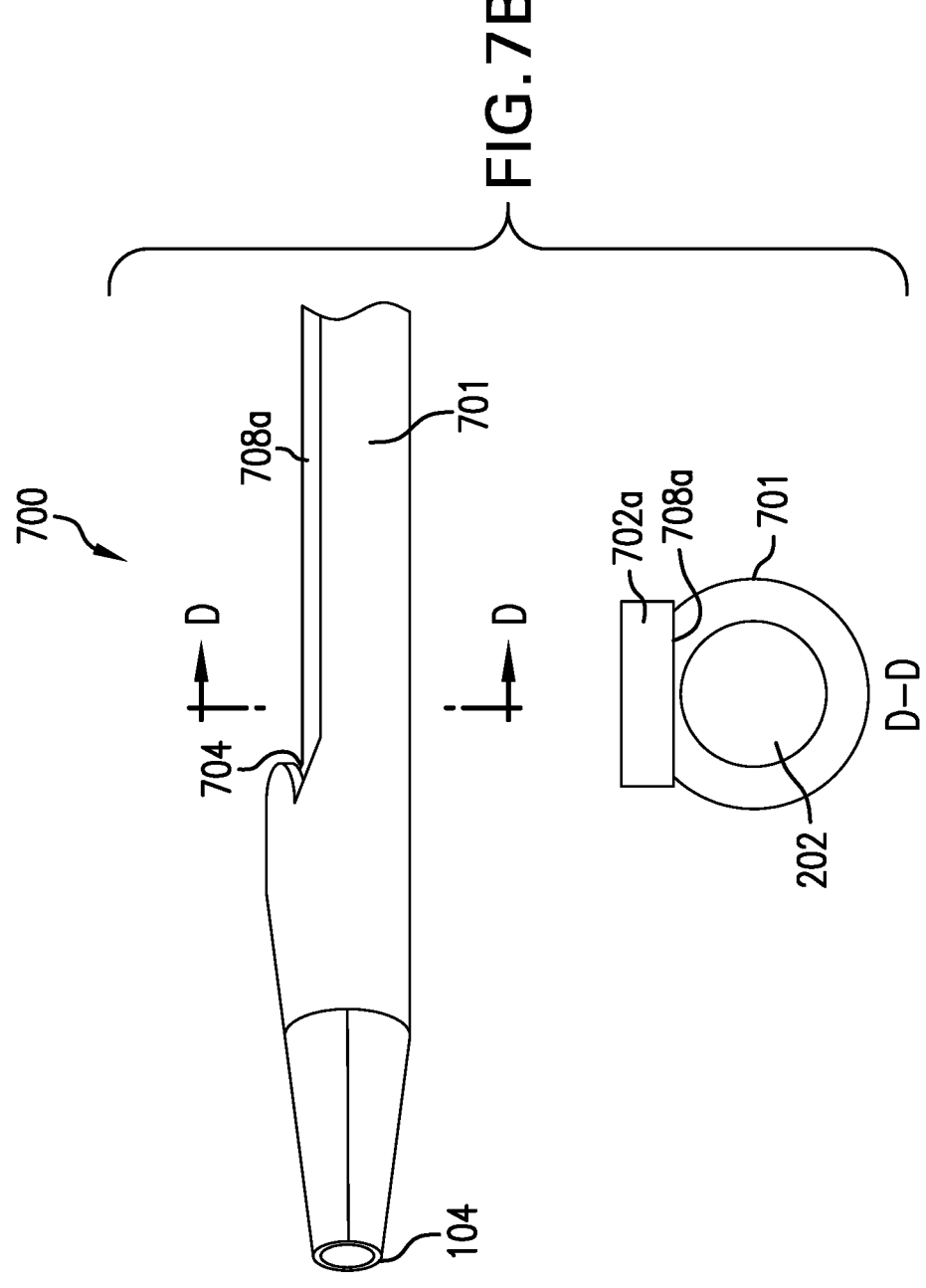

FIGS. 7A and 7B include exemplary illustrations that include a pseudo-perspective view along with at least one cross-section view of alternative embodiments of cannulas 700 configured to accommodate one or more sensors 702a/702b in accordance with embodiments of the present invention. In FIG. 7A the cannula 700 includes the body 701 along with the tip 114 and the distal end 104. In view A-A, looking at the distal end 104, an opening 703 is illustrated as being circular. The circular opening 703 should not be construed as limiting as opening 703 in alternative embodiments may have other shapes such as, but not limited to ovals or polygons. In previously discussed embodiments the tip 114 tapered to a smaller size from the body distal 108 to the distal end 104. In the embodiments shown in FIG. 7A the tip 114 includes dual tapers. A first taper from the body distal 108 toward the distal end 104 results in a portion of the tip having a larger size 706 than the body 701. A second taper from the larger size 706 toward the distal end 104 results in the distal end 104 being smaller than the body 701. In other embodiments, the distal end 104 may be larger, similar in size or the same size as the body 701.

The larger size 706 portion of the tip 114 can enable the formation of the undercut 704 that is configured to retain a portion of the sensor 702*a*. In many embodiments the undercut 704 can be construed as a pocket formed between the body 701 and the tip 114. The pocket, or undercut 704 enables a portion of a sensor to be removably coupled with the cannula 700.

In FIG. 7A the body 701 includes flats 708*a* and 708*b* rather than channels as discussed in previous embodiments. The flats 708*a*/708*b* can be formed during an extrusion process that forms the body 701. As shown in sections B-B and C-C, when a portion of the sensors 702*a*/702*b* is secured within the undercut 704, the sensors 702*a*/702*b* are intended to be positioned upon the flats 708*a*/708*b*. Placement of the sensors 702*a*/702*b* against the flats 708*a*/708*b* rather than within a channel can enable improved exposure to fluid containing the analyte to be measured when the cannula and sensor are implanted within a subject.

The embodiment in FIG. 7B differs from FIG. 7A in that the cannula 700 includes a single undercut 704. The inclusion of a single pocket within the cannula 700 enables a single sensor 702*a* to be coupled with the cannula 700. Having only one pocket, or undercut 704, can enable a reduction in size of the tip relative to embodiments having two undercuts. Reducing the overall size of the tip can reduce insertion force resulting in improved user comfort and less apprehension of pain often associated with insertion of subdermal sensors and cannulas.

Sensors or sensor assemblies described above, when used with cannula assemblies, may both (1) sense at least one analyte and/or physiological property and (2) deliver at least one infusate, using a single implantation site. A single implantation site may use less space and may cause less trauma.

Furthermore, "sensor" or "sensor assembly" as used herein is any device, component or combination that (1) detects/records/communicates information about an event or the presence/absence of a particular analyte, thing or property in its sensing environment, and/or (2) indicates an absolute or relative value/quantity/concentration, or rate of change, of that analyte, thing or property.

The sensor may be based on any principle and can be an electrochemical sensor, an impedance sensor, an acoustic sensor, a radiation sensor, a flow sensor, an immunosensor, or the like. For in-vivo use in medical and veterinary applications, the sensor may be used to detect, measure and/or record (1) one or more analytes, such as, but not limited to glucose, lactate, oxygen, ketone, or any other marker(s) of a disease or medical condition, and (2) one or more of properties, such as temperature, pressure, perfusion rate, hydration or pH.

The use of the sensing and infusion devices described herein are also not limited to a specific physical structure of the sensor or infusion device. For example, in a glucose sensing application, the sensor may be similar to a conventional glucose sensors that use a glucose-limiting membrane and generally based on the principles of one-dimensional diffusion, where glucose and oxygen travel in the same general direction before reacting within the enzyme layer (e.g., glucose oxidase) at the working electrode. Or the sensor can use any other non-conventional structure, based on a glucose sensor without a glucose limiting membrane and/or any structure that takes advantage of multi-dimensional diffusion.

The combined sensing/infusion devices described herein may be applied in any medical or veterinary application. This includes the treatment/management of diabetes and the development of the artificial pancreas, by having a single point of insertion for infusion and sensing that reduces trauma to the patient; the embodiments described herein would allow one or more glucose sensors to be placed within one or more infusion catheters that deliver one or more drugs/agents/infusates (e.g., glucagon and insulin). The combined sensing/infusion devices can also be used to support organ failure with sensor augmented drug delivery, by combining an infusion catheter with sensors (e.g., sensors for lactate and oxygen) and directly inserting the device in the vasculature and tissue of failing organs, thereby providing high dose, targeted therapy designed to normalize mitochondria function. Alternatively, it can also be used to monitor metabolic changes in current or former cancer patients and tailor treatment compositions based on metabolic profiling specific to a cancer type.

In many embodiments, additional features or elements can be included or added to the exemplary features described above. Alternatively, in other embodiments, fewer features or elements can be included or removed from the exemplary features described above. In still other embodiments, where possible, combination of elements or features discussed or disclosed incongruously may be combined together in a single embodiment rather than discreetly as in the exemplary discussion. Accordingly, while the description above refers to particular embodiments of the invention, it will be understood that many modifications or combinations of the disclosed embodiments may be made without departing from the spirit thereof. The presently disclosed embodiments are therefore to be considered in all respects as illustrative and not restrictive.

The invention claimed is:

1. An integrated cannula and sensor assembly, comprising:

a cannula having a proximal end, a distal end, and a fluid path within the cannula, the cannula further having a body, the body including both a body distal being defined between the proximal end and the distal end and a channel located on an exterior of the cannula, the channel having a base defined as a face opposite the fluid path, the channel further having a first cannula locating feature that extends away from the base and protrudes into the channel;

a tip being coupled to the body distal of the cannula; and a sensor assembly being located within the channel on the exterior of the cannula, the sensor assembly having a sensor proximal end and a sensor distal end, wherein the coupling of the tip to the body distal defines a distal end undercut configured to retain only the sensor distal end of the sensor assembly, the distal end undercut not intersecting the fluid path.

2. The integrated cannula and sensor assembly of claim 1, further comprising:

the first cannula locating feature being a boss feature; and a first sensor locating feature on the sensor assembly, the first sensor locating feature enabling coupling of the sensor the sensor to the first cannula locating feature, the first sensor locating feature being an aperture formed through the sensor.

3. The integrated cannula and sensor assembly of claim 2, wherein a tipping operation couples the tip to the body.

4. The integrated cannula and sensor assembly of claim 3, wherein the tipping operation further creates the first cannula locating feature.

5. The integrated cannula and sensor assembly of claim 4, wherein the aperture through the sensor assembly is configured to receive the boss feature.

6. The integrated cannula and sensor assembly of claim 5, wherein the boss feature is deformed to couple the sensor assembly to the cannula via the aperture through the sensor assembly.

7. The integrated cannula and sensor assembly of claim 2, further comprising:

a first cannula key feature being formed within the cannula; and a first sensor key feature being formed on the distal end of the sensor assembly, the first sensor key feature interfacing with the first cannula key feature to orient the sensor assembly relative to the cannula.

8. The integrated cannula and sensor assembly of claim 1, further comprising:

a first cannula key feature being formed within the cannula; and a first sensor key feature being formed on the distal end of the sensor assembly, the first sensor key feature interfacing with the first cannula key feature to orient the sensor assembly relative to the cannula.

9. The integrated cannula and sensor assembly of claim 8, wherein the first cannula key feature is formed during a tipping operation that couples the tip to the body.

10. An integrated cannula and sensor assembly, comprising:

a cannula having a proximal end, a distal end, and a fluid path within the cannula, the cannula further having a body and a tip, the body including a first channel being located on an exterior of the cannula, a second channel also being located on the exterior of the cannula, and a body distal being between the proximal end and the distal end, the tip being between the body distal and the distal end, the first channel having a first cannula locating feature that extends away from a first channel base of the first channel, the second channel having a second cannula locating feature that extends away from a second channel base of the second channel; and a first sensor assembly being located within the first channel, the first sensor assembly having first distal end;

a second sensor assembly being located within the second channel, the second sensor assembly having a second distal end;

wherein the tip further includes a first distal end undercut that retains only the first distal end of the first sensor assembly and a second distal end undercut that retains only the second distal end of the second sensor assembly, both the first and second sensor assemblies not intersecting the fluid path.

11. The integrated cannula and sensor assembly of claim 10, wherein the body and the tip are permanently coupled together during a tipping operation.

12. The integrated cannula and sensor assembly of claim 11, further comprising:

the first cannula locating feature and being a boss feature;

a first sensor locating feature being formed on the first sensor assembly, the first sensor locating feature being an aperture formed through the first sensor assembly, the first sensor locating feature enabling coupling of the first sensor assembly to the first cannula locating feature.

13. The integrated cannula and sensor assembly of claim 12, further comprising:

the second cannula locating feature being a boss feature; and a second sensor locating feature being formed on the second sensor assembly, the second sensor locating feature being an aperture formed through the second sensor assembly, the second sensor locating feature enabling coupling of the second sensor assembly to the second cannula locating feature.

14. The integrated cannula and sensor assembly of claim 13, wherein the first sensor locating feature is different from the second sensor locating feature.

15. The integrated cannula and sensor assembly of claim 12, further comprising:

a first cannula key feature being formed within the body distal of the cannula; and a first sensor key feature being formed on the distal end of the first sensor assembly, the first sensor key feature interfacing with the first cannula key feature to orient the first sensor assembly relative to the cannula.

16. The integrated cannula and sensor assembly of claim 10, further comprising:

a first cannula key feature being formed within the body distal of the cannula; and a first sensor key feature being formed on the distal end of the first sensor assembly, the first sensor key feature interfacing with the first cannula key feature to orient the first sensor assembly relative to the cannula.

17. The integrated cannula and sensor assembly of claim 16, further comprising:

a second cannula key feature being formed within the body distal of the cannula; and a second sensor key feature being formed on the distal end of the second sensor assembly, the second sensor key feature interfacing with the second cannula key feature to orient the second sensor assembly relative to the cannula.

18. The integrated cannula and sensor assembly of claim 17, wherein the first key feature is different from the second key feature.

* * * * *